United States Patent [19]

Geysen

[11] Patent Number: 4,708,871

[45] Date of Patent: Nov. 24, 1987

[54] ANTIGENICALLY ACTIVE AMINO ACID SEQUENCES

[75] Inventor: Hendrik Geysen, Knoxfield, Australia

[73] Assignee: Commonwealth Serum Laboratories Commission, Parkville, Australia

[21] Appl. No.: 674,907

[22] PCT Filed: Mar. 8, 1984

[86] PCT No.: PCT/AU84/00038

§ 371 Date: Nov. 8, 1984

§ 102(e) Date: Nov. 8, 1984

[87] PCT Pub. No.: WO84/03506

PCT Pub. Date: Sep. 13, 1984

[30] Foreign Application Priority Data

Mar. 8, 1983 [AU] Australia ............................ PF8347

[51] Int. Cl.$^4$ ................... A61K 39/00; C07K 7/06; G01N 53/00

[52] U.S. Cl. .................................... 424/88; 530/329; 435/7

[58] Field of Search .................. 530/329, 324; 424/88; 435/7

[56] References Cited

U.S. PATENT DOCUMENTS 4,544,500 10/1985 Bittle et al. ........................ 530/324
4,554,101 11/1985 Hopp .................................. 530/329
4,605,512 8/1986 Schaller et al. ..................... 530/326

Primary Examiner—Delbert R. Phillips
Attorney, Agent, or Firm—Sughrue, Mion, Zinn, Macpeak, and Seas

[57] ABSTRACT

A synthetic peptide which displays the antigenicity of the VP1 protein of foot-and-mouth disease virus, characterised in that at least a portion of said peptide is selected from the group consisting of five-, six- or seven-long antigenically active amino acid sequences of said VP1 protein, and antigenically active modified sequences thereof.

18 Claims, 13 Drawing Figures

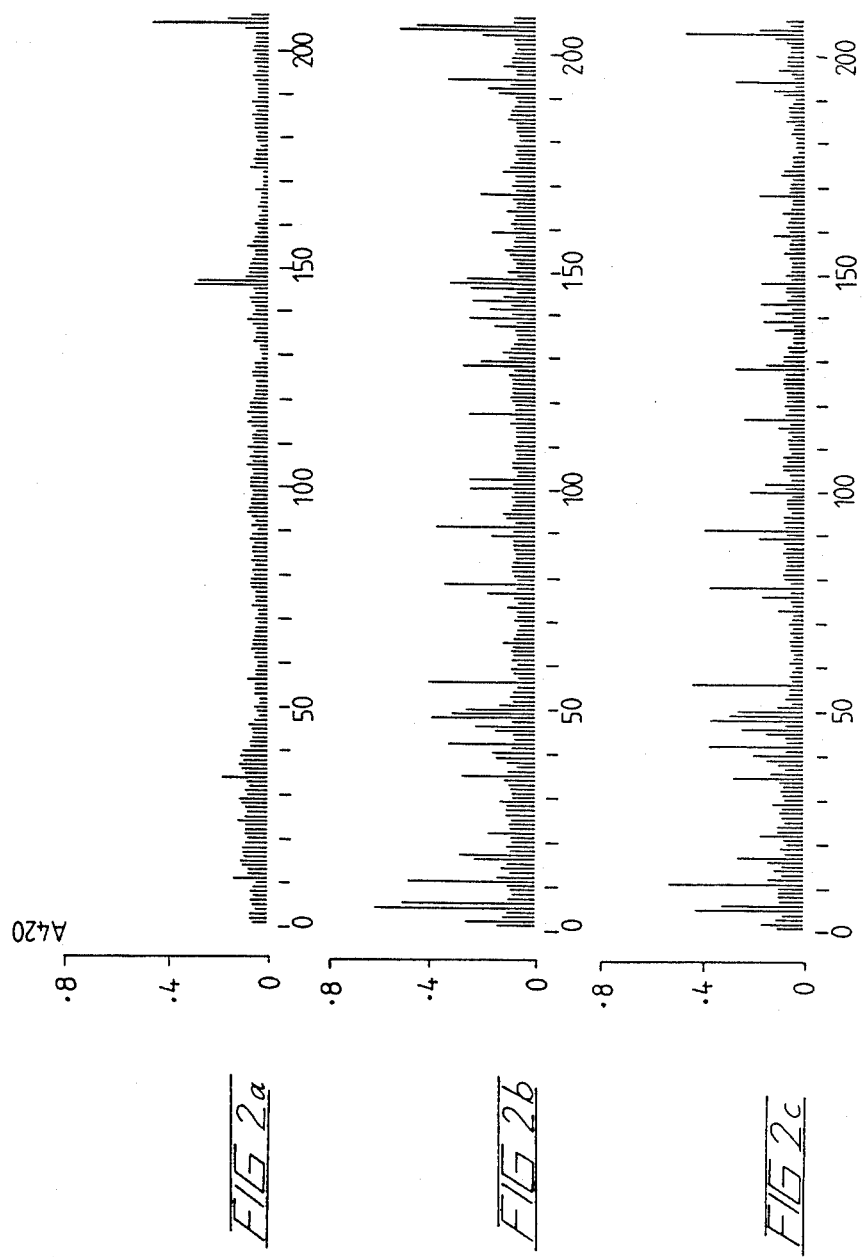

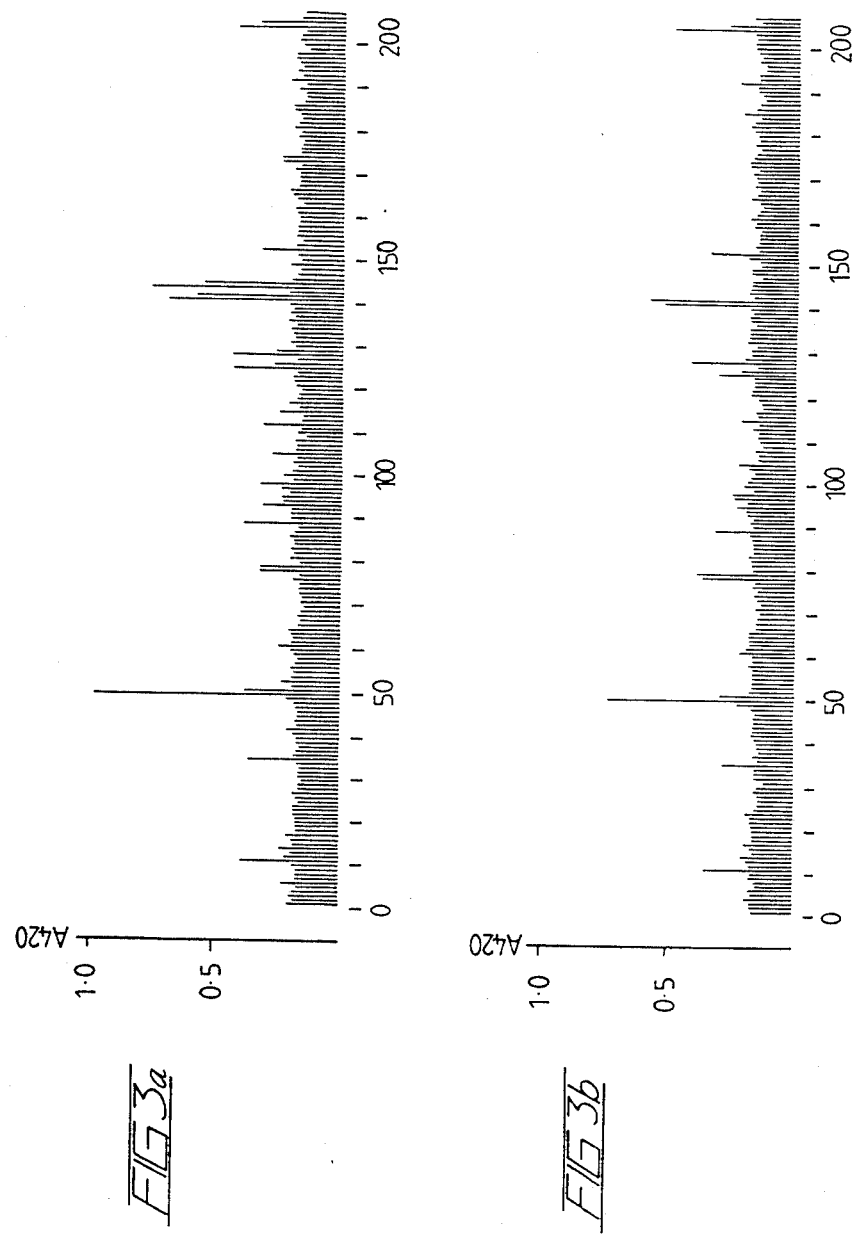

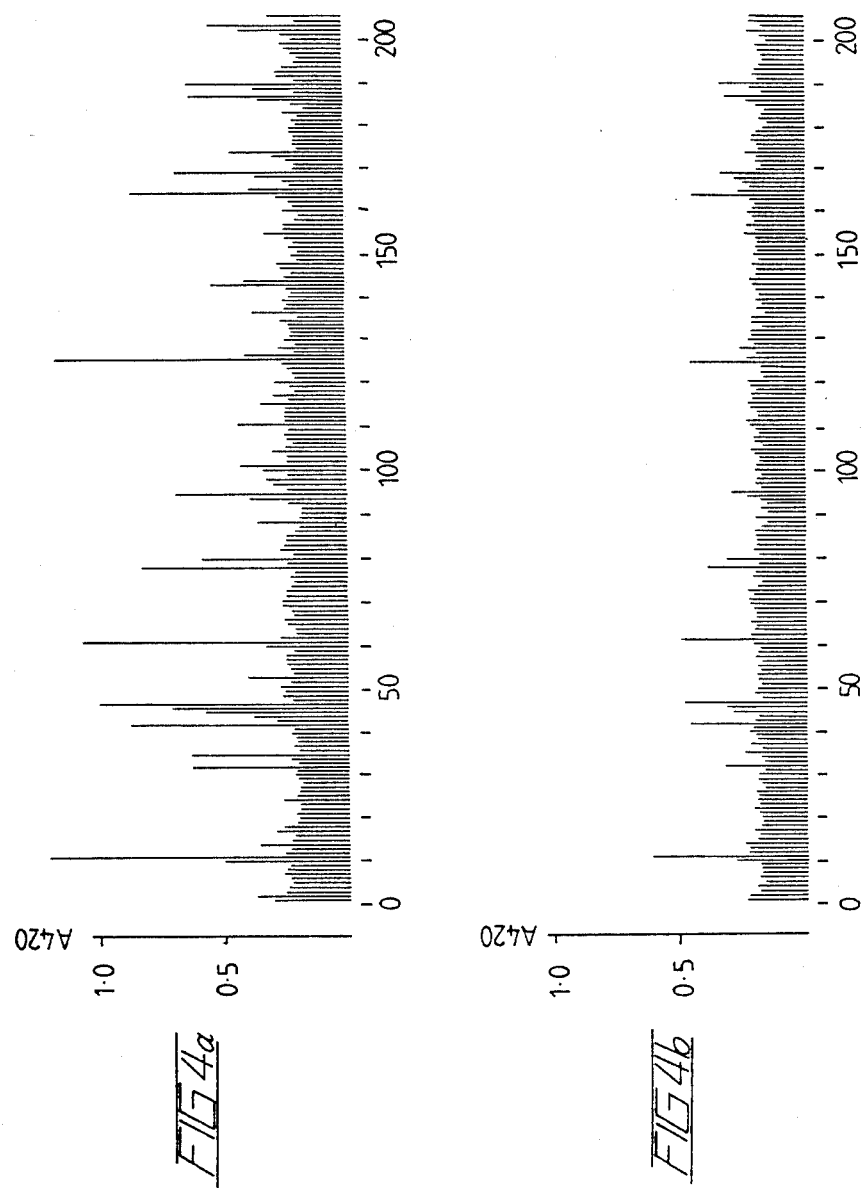

```
                    135                                        155
                    |                                          |
FMDV, Type A₁₀   K-Y-S-A-S-D-S-R-S-G-D-L-G-S-I-A-A-R-V-A-T
FMDV, Type O₁    R-Y-N-R-N-A-V-P-N-L-R-G-D-L-Q-V-L-A-Q-K-V
FMDV, Type C₁    T-Y-T-A-S-T-R-G-D-L-A-H-L-T-A-T-R-A-G-H-L
```

Systematic substitution at each location by all alternative naturally occurring amino acids Ac-NH-( *-*-*-*-*-* )-A-K-NH-PPA
                              |
                              OMe

[Chromatogram with x-axis labels: G, D, L, Q, V, L; y-axis A₄₂₀ from 0 to 1.0]

ANTIGENICALLY ACTIVE AMINO ACID SEQUENCES

This invention relates to the identification and chemical synthesis of peptides (or amino acid sequences) which constitute the immunogenic determinant(s) of an immunologically important coat protein, VP1, of foot-and-mouth disease virus, and to the use of these peptides for example, in the production of vaccines and diagnostic reagents.

In the search for more effective means of protection against infective disease in man and animals, major advances have been made in the last decade. It is now clear that immunization is possible using an isolated component of the whole causative agent, such as for example in the influenza virus sub-unit vaccines.

Current efforts are directed at reducing the scale of the immunizing component still further, first to the polypeptide (protein) carrying the necessary trigger for the immune system and secondly to the trigger itself. Recombinant DNA technology has provided the means, by translation from the determined nucleotide sequences, of obtaining reliable amino acid sequences for biologically important proteins including such proteins which were not readily available from natural sources. However, methods for identifying the loci of a protein which constitute the trigger(s) or immunogenic determinant(s) are few and very time consuming and form the bottle neck to further rapid progress The determination of the immunogenic determinant(s) for biologically important proteins, particularly proteins derived from the causative agents of infective disease in man and animals, is regarded as being of particular importance since, once these determinants have been identified, they can be simply and economically synthesised so as to provide the desired peptide sequences for use in vaccines which will have a high degree of specificity, and which will avoid any undesired effects from unnecessary amino acid or peptide sequences which might still be present in, for example, sub-unit type vaccines.

The immunogenicity of a polypeptide can be defined as the immune response directed against a limited number of immunogenic determinants, which are confined to a few loci on the polypeptide molecule, (see Crumpton, M. J., in The Antigens (ed. Sela, M., Academic Press, New York, 1974); Benjamini, E. et al., Curr. Topics Microbiol. Immunol. 58 85–135 (1972); and Atassi, M. Z., Immunochemistry 12, 423–438 (1975).) Antisera prepared against chemically synthesized peptides corresponding to short linear stretches of the polypeptide sequence have been shown to react well with the whole polypeptide, (see Green, N. et al., Cell 28, 477–487 (1982); Bittle, J. L. et al., Nature 298, 30–33 (1982); Dreesman et al., Nature 295, 158–160 (1982); Prince, A. M., Ikram, H., Hopp, T. P., Proc. Nat. Acad. Sci. USA 79, 579–582 (1982); Lerner, R. A. et al., Proc. Nat. Acad. Sci. USA 78, 3403–3407 (1981); and Neurath, A. R., Kent, S. B. H., Strick, N., Proc.Nat.Acad.Sci. USA 79, 7871–7875 (1982).) However, interactions have been found to occur even when the site of interaction does not correlate with the immunogenic determinants of the native protein, (see Green, N., et al, Supra). Conversely, since antibodies produced against the native protein are by definition directed to the immunogenic determinants, it follows that a peptide interacting with these antibodies must contain at least a part of an immunogenic determinant.

From a study of the few proteins for which the immunogenic determinants have been accurately mapped, it is clear that a determinant can consist of a single sequence, (continuous), or of several sequences (discontinuous) brought together from linearly distant regions of the polypeptide chain by the folding of that chain as it exists in the native state, (see Atassi, M. Z., Immunochemistry 15, 909–936 (1978).). As in the case of lysozyme several of the elements consist of only one amino acid, the size of a contributing element can then vary between one and the maximum number of amino acids consistent with the dimensions of the antibody combining site, and is likely to be of the order of five to six, (see Atassi, M. Z., supra). Any systematic mapping of all the detectable antigenic elements of a polypeptide by the chemical synthesis of overlapping segments and measurement of their subsequent reactivity with antisera prepared against the native protein has until now been severely limited by the scale of the synthetic and testing capability required, (see Atassi, M. Z., supra, and Kazim, A. L., Atassi, M. Z., Biochem.J. 191, 261–264 (1980)).

The precise localisation of immunogenic determinants within the amino acid sequence of a few proteins has been performed by one or more of the following approaches: (1) antigenicity measurements of the whole polypeptide or peptide fragments isolated therefrom, before and after chemical modification at specific residues; (2) locating the position, within the polypeptide amino acid sequence of substitutions, selected by growing the virus expressing the protein in the presence of monoclonal antibodies; and (3) synthesis and testing of peptides, homologous with the amino acid sequence, of regions suspected of immunogenic activity. This last method probably gives the best opportunities for a comprehensive approach; however, the synthesis and purification of numerous peptides requires a great deal of expertise and time. Smith, J. A., et al, Immunochemistry 14, 565–568 (1977), circumvented the decoupling and purification steps by combining solid-phase peptide synthesis and solid-phase radio-immune assay using the same solid support, (see also Hurrell, J. G. R., Smith, J. A., Leach, S. J., Immunochemistry 15, 297–302 (1978)). With this procedure they were able to confirm the locations of the continuous immunogenic determinants of two proteins. However, even with this simplified approach, any systematic scan for antibody-binding activity of all possible hexapeptides from even a relatively small protein such as Virus Protein 1 (VP1) of foot-and-mouth disease virus (FMDV) which is known to have 213 amino acids, would take an unacceptably long time.

The FMD virus, which belongs to the aphthovirus genus of the family Picornaviridae, consists of an ordered aggregation of structurally independent sub-units surrounding a molecule of infectious single-stranded RNA. Under relatively mild conditions the whole particle readily dis-aggregates to give the naked RNA, 60 copies of the VP4 polypeptide, and 12 sub-units consisting of an ordered arrangement of five copies of each of the polypeptides, VP1, VP2 and VP3. Each of these structural sub-units can be further disrupted to yield the isolated component proteins. The VP1 protein of FMD virus has been shown to be an immunologically important coat protein of the virus.

Following the development of new techniques for the solid-phase synthesis of peptides, it has now become possible to develop a method for the concurrent synthesis on solid supports of hundreds of peptides. Interaction of synthesized peptides with antibodies is then easily detected without removing them from the support. A preferred method for solid-phase synthesis according to the present invention comprises the use of a polymeric material such as polyethylene or polypropylene as the solid-phase carrier, onto which is graft polymerised a vinyl monomer containing at least one functional group to produce polymeric chains on the carrier. The functional groups of these polymeric chains are then reacted to provide primary or secondary amino groups of the chains, and these amino groups are then sequentially reacted with amino acid residues in appropriate order so as to build up a desired synthetic peptide. The carrier is preferably in the form of a solid polymer rod having a diameter of about 4 mm and a length of about 50 mm. A number of such rods can be held in a suitable holder in a 12×8 grid whose dimensions correspond to those of the standard microtitre plate used for enzyme-linked immunosorbent assays (ELISA).

As a result of work now carried out using the above technique, peptides which constitute immunogenic determinant(s) of the VP1 coat proteins of a number of important serotypes of foot-and-mouth disease virus have been identified and chemically synthesized.

Note: Throughout this specifiction amino acid residues will be denoted by the three-letter abbreviation or single-letter code as follows:

| Amino Acid | Three-letter abbreviation | One-letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In broad terms, the present invention provides a synthetic peptide which displays the antigenicity of the VP1 protein of foot-and-mouth disease virus, characterised in that at least a portion of said peptide is selected from the group consisting of five-, six- or seven-long antigenically active amino acid sequences of said VP1 protein, and antigenically active modified sequences (as hereinafter defined) thereof.

According to a first aspect of the present invention, there is provided a synthetic peptide which displays the antigenicity of the VP1 protein of foot-and-mouth disease virus, Type $O_1$, characterised in that at least a portion of said peptide is selected from amino acid sequences of the group consisting of:
(i) G - D - L - Q - V - L - A;
(ii) G - D - L - Q - V - L;
(iii) D - L - Q - V - L - A;
(iv) D - L - Q - V - L; and
(v) antigenically active modified sequences (as hereinafter defined) based on any one of the sequences (i) to (iv) above.

According to a second aspect of the present invention, there is provided a synthetic peptide which displays the antigenicity of the VP1 protein of foot-and-mouth disease virus, type $A_{10}$ ($A_{61}$), characterised in that at least a portion of said
(ii) G - D - L - Q - V - L; peptide is selected from amino acid sequences of the group consisting of:
(i) G - D - L - G - S - I - A;
(ii) G - D - L - G - S - I;
(iii) D - L - G - S - I - A;
(iv) D - L - G - S - I; and
(v) antigenically active modified sequences (as hereinafter defined) based on any one of the sequences (i) to (iv) above.

According to a third aspect of the present invention, there is provided a synthetic peptide which displays the antigenicity of the VP1 protein of foot-and-mouth disease virus, type C1, characterised in that at least a portion of said peptide is selected from amino acid sequences of the group consisting of:
(i) D - L - A - H - L - T - A;
(ii) D - L - A - H - L - T;
(iii) L - A - H - L - T - A;
(iv) L - A - H - L - T; and
(v) antigenically active modified sequences (as hereinafter defined) based on any one of the sequences (i) to (iv) above.

The term "antigenically active modified sequences" as used herein, is used to describe sequences of amino acids which are based on any one of sequences (i) to (iv) of the first, second or third aspects of the invention as described above, but in which one of the amino acids in the said sequence is replaced by another amino acid to provide a modified sequence which is antigenically active.

A brief description of the figures to follow is set forth below:

FIGS. 2a, 2b, 2c, 2d, 2e and 2f show antigenic profiles of the hexapeptides prepared in Example 1.

Figure 1:
FIG. 1 shows the synthesis of the 213-amino acid sequence of VP1 with a 2-long amino acid spacer.

FIGS. 3a, and 3b show the antigenic profiles of the hexapeptides of Example 2.

FIGS. 4a, and 4b show anitgenic profiles for the hexapeptides of Example 3.

FIG. 5 shows diagrammatically the synthesis strategy employed in Example 4.

FIG. 6 shows the antibody-binding activity of the peptides described in Example 4.

Antigenically active modified sequences in accordance with the first aspect of this invention include hexapeptide sequences based on the formula:

$$\begin{array}{cccccc} G\!-\!D\!-\!L\!-\!Q\!-\!V\!-\!L \\ (1) & (2) & (3) & (4) & (5) & (6) \end{array}$$

in which:

G at position (1) is replaced by A, H, I, K, M, N, P, Q, S or T; or

D at position (2) is replaced by A, C, E, F, G, H, I, K, L, M, N, P, Q, R, S, T, V or Y; or Q at position (4) is replaced by D, K, A, M, E, N, S or R; or V at position (5) is replaced by A, D, E, F, I, K, L, M, N, Q, R, S, T or Y.

Antigenically active modified sequences in accordance with the second aspect of this invention include hexapeptide sequences based on the formula:

$$G-D-L-G-S-I$$
$$(1)\ (2)\ (3)\ (4)\ (5)\ (6)$$

in which:

G at position (1) is replaced by A, C, D, E, F, H, I, K, L, M, N, P, Q, R, S, T, V, W or Y; or D at position (2) is replaced by L; or G at position (4) is replaced by A; or S at position (5) is replaced by T, G or A; or I at position (6) is replaced by A, C, D, E, F, K, L, M, Q, R, S, T, V, W or Y.

Antigenically active modified sequences in accordance with the third aspect of this invention include hexapeptide sequences based on the formula:

$$D-L-A-H-L-T$$
$$(1)\ (2)\ (3)\ (4)\ (5)\ (6)$$

in which:

D at position (1) is replaced by H or V; or

H at position (4) is replaced by A, C, D, E, F, K, L, M, N, Q, R, S, T, V or Y; or T at position (6) is replaced by S.

In arriving at this invention, the concurrent chemical synthesis of all possible hexapeptides representing the total sequences of the VP1 coat proteins of FMD virus, types $O_1$, $A_{10}$ (or $A_{61}$) and $C_1$, with the overlap of five amino acids between peptides in juxtaposition in the sequence has been completed using the solid-phase synthesis technique described above. The synthetic peptides, still attached to the support used for their synthesis, have been tested for antibody-binding activity by ELISA to produce a complete map of all the reactive sequences of the VP1 proteins at a resolution of six amino acids. A peptide length of six amino acids was chosen, taking into account the following factors:

1. antibody interactions with hexapeptides have been demonstrated;

2. the longer a peptide the greater the possibility of its folding with a secondary structure, this folding not necessarily being that occurring in the native protein;

3. during synthesis the yield of the desired peptide decreases as the number of coupling reactions increases; and 4. the smaller the sequence synthesized the greater the precision in specifying the bounds of a detected active sequence within the whole sequence.

As set out above, the peptides of the present invention are characterised in that at least a portion of the peptide contains an amino acid sequence selected from the groups (i) to (v) described above. Tests which have been carried out, particularly utilising the ELISA technique, have established the activity of these amino acid sequences by their reactivity with antisera. It should be noted, however, that whilst the synthetic peptides of this invention may comprise sequences which are only 5, 6 or 7 amino acids long, the present invention also extends to synthetic peptides in which one or more additional amino acids are included on either or both ends of the defined sequence, that is either on the carboxyl (—COOH) end or on the amino (—NH$_2$) end or both. While such additional amino acids may not play any direct role in enhancing the immunogenic activity of the defined amino acid sequence, they may act, for example, as spacer amino acids to space the antigenically active amino acid sequence from the free carboxyl and/or free amino ends of the sequence.

Following identification of the antigenically active amino acid sequences of the VP1 proteins, the modified sequences in accordance with this invention have been similarly synthesised and tested utilising the ELISA technique. As previously described, each of these modified sequences was derived by replacing one amino acid in the original sequence by another amino acid.

The peptides of the present invention can be chemically synthesized from their constituent amino acids. This synthesis may be carried out, for example, by the Merrifield solid-phase method, as described in J.A.C.S. 85: 2149–2154 (1963). In the Merrifield solid-phase method, the C-terminal amino acid is attached to chloromethylated polystyrene-divinylbenzene copolymer beads. Each subsequent amino acid, with a suitable protecting group if necessary, is then added sequentially to the growing chain. As described in the Merrifield article, the protective group may be, for example, a t-butyloxycarbonyl or carbobenzoxy group. By the procedure of coupling, deprotection, and coupling of the next amino acid, the desired amino acid sequence and chain length can be produced. As a final step, the protective group is removed from N-terminal amino acid, and the C-terminal amino acid is cleaved from the supporting beads, using a suitable reagent such as trifluoroacetic acid and hydrogen bromide. Alternatively, the synthesis can be carried out by the solid-phase method, in which the synthetic peptide structure is built up on a solid-phase carrier which comprises a polymeric material, for example a polyethylene rod or pin, having a vinyl monomer graft polymerised thereto, for example by γ-radiation of acrylic acid, acrylonitrile or acrylamide monomers. A mono- protected biamine such as lysine or lysine-alanine is then reacted with the polymeric chain formed on the solid-phase carrier and the synthetic peptide then built up by sequential reaction of amino acids in the same manner as in the Merrifield method described above.

It should be noted that whilst the final step in both the methods referred to above is the removal of the synthetic peptide from the solid-phase carrier or support by a cleaving reaction using a suitable reagent, for some uses of the peptides of the present invention it is convenient if not essential for the chemically synthesized peptides to be used in the form of a product in which the peptide is coupled or linked to a solid-phase carrier or support. For such uses, of course, the final cleaving step is omitted. Such antigenically active, chemically synthesized peptides which are immobilised on a solid-phase carrier or support are of particular utility in the performance of immunochemical assays, such as enzyme immunoassays (EIA).

The immunogenic synthetic peptides of the present invention may provide the basis upon which the formation of synthetic vaccines against foot-and-mouth disease virus can be developed. Such synthetic vaccines would have particular merit insofar as they could be manufactured so as to be free of amino acid sequences corresponding to the entire amino acid sequences of the viral protein, and also free of biologically produced materials and of active or inactivated viral residues. The use of synthetic peptides as the basis for vaccines is discussed, for example, by Beale, J. in Nature 298 14–15

(1982), and by Sutcliffe, J. G. et al in Science, 219, 660–666 (1982). In formation of a synthetic vaccine, the synthetic peptides of the present invention could be used either alone, in combination, and/or in association with a physiologically acceptable carrier and/or adjuvant. The synthetic peptides of the present invention also have potential for use in a number of other applications in the immunological field, including use in diagnostic and other immunological testing procedures, particularly in immunochemical assays such as enzyme immunoassays.

Further details of the peptide compounds of this invention, their method of preparation and their antigenic activity are illustrated by the following Examples:

EXAMPLE 1

A. Preparation of hexapeptides

The 213-amino acid sequence of VP1 (FMDV, type $O_1$) as translated by Kurz, C. et al., Nucleic Acid Research 9, 1919–1931 (1981) was subdivided into all possible hexapeptide units, and each hexapeptide unit was synthesized on a polyethylene support in the same orientation, and with a 2-long amino acid spacer as illustrated in FIG. 1.

Polyethylene rods immersed in a 6% v/v aqueous solution of acrylic acid were γ-ray irradiated at a dose of 1 Mrad (see Muller-Schulte, D., Horster, F. A., Polymer Bulletin 7, 77–81 (1982)). Using conventional methods of solid-phase peptide chemistry (see Erickson, B. W., Merrifield, R. B. in "The Proteins", Vol. 2, 255–257, Academic Press, New York (1976); Meienhofer, J., in "Hormonal Proteins and Peptides", Vol.2. 45–267, Academic Press, New York (1973)), $N^{\alpha}$-t-Butyloxycarbonyl-L-Lysine methyl ester was coupled to the polyethylene polyacrylic acid (PPA) via the N-amino group of the side-chain. This was followed by the coupling of Boc-Alanine, to complete a peptide-like spacer. Amino-substitution of the support was determined by reacting $NH_2$-Lysine(OMe)-PPA with $C^{14}$ labelled butyric acid, and was found to be 8–10 nmoles/rod.

Successive amino acids were added by conventional solid phase peptide synthesis as dictated by the sequence to be synthesized. At the completion of the final coupling reaction, and after removal of the t-butyloxycarbonyl (Boc) protecting group, the terminal amino group was acetylated with acetic anhydride in a dimethylformamide(DMF)/triethylamine mixture. All dicyclohexyl carbodiimide-mediated coupling reactions were carried out in DMF in the presence of N-hydroxy benzotriazole. The following side-chain protecting groups were used; O-benzyl for threonine, serine, aspartic acid, glutamic acid and tyrosine; carbobenzoxy for lysine; tosyl for arginine; 4-methyl benzyl for cysteine and 1-benzyloxycarbonylamido-2,2,2,-trifluoroethyl for histidine. Side-chain deprotection was achieved by treatment with borontris(trifluoroacetate) in trifluoroacetic acid for 90 minutes at room temperature (see Pless, J., Bauer, W., Angewante Chemie 85, 142 (1973)). After hydrolysis in HCl/propionic acid, analysis of sequences included in the synthesis as controls confirmed that coupling at each stage had occurred. Before testing by ELISA, rod-coupled peptides were washed several times in phosphate buffered saline (PBS).

B. Testing of Hexapeptides

Figures 2D, 2E, 2F:
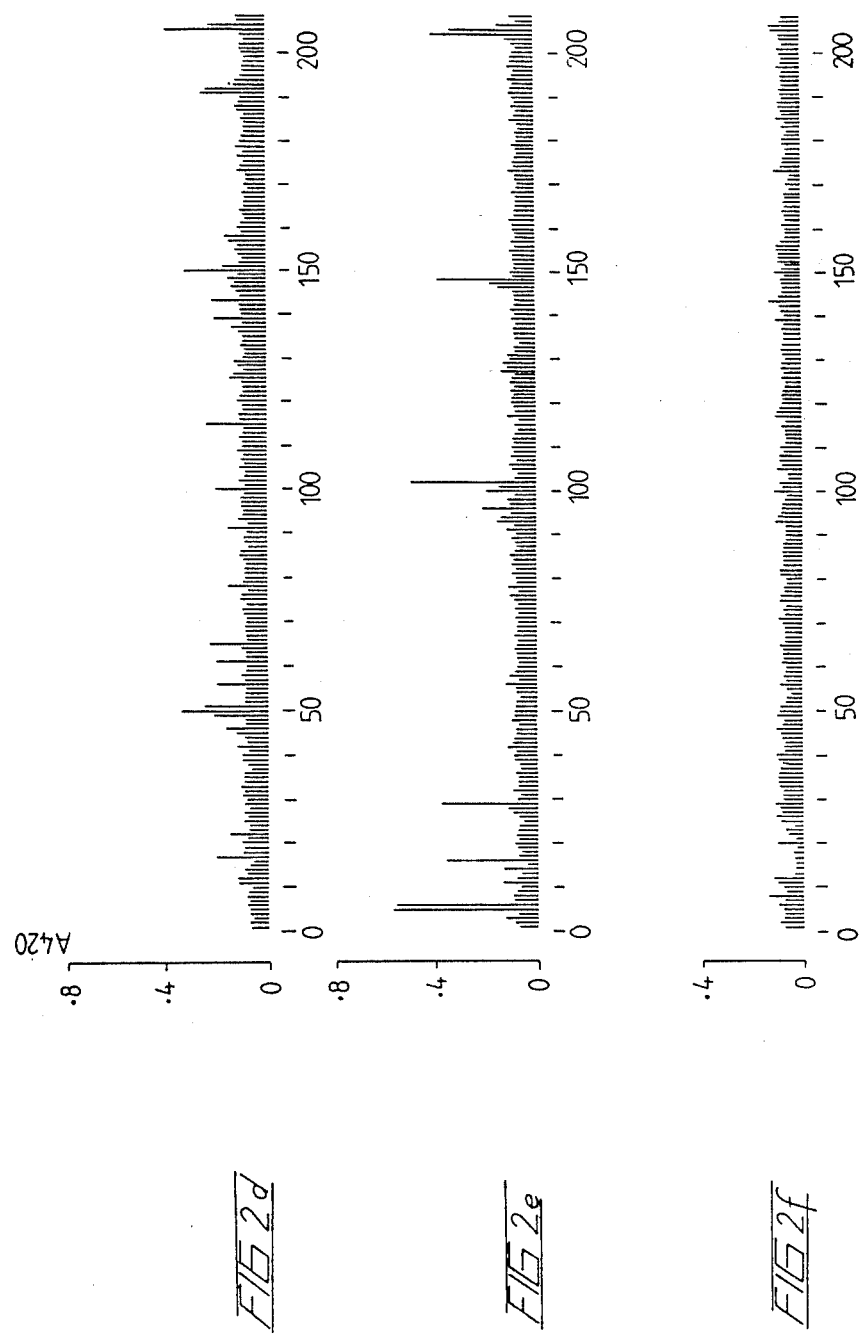

Antigenic profiles for the hexapeptides prepared as described in A. above are shown in FIG. 2 as a vertical line proportional to the ELISA extinction obtained, over the number giving the location within the VP1 sequence of the peptide N-terminal amino acid. Antisera used to produce the different profiles as shown, were as follows:

(a) and (b) two different anti-intact virus particle, type $O_1$;
(c) anti-intact virus particle, as used in (b), after absorption with purified complete virus, type $O_1$;
(d) anti-virus-subunit, type $O_1$;
(e) anti-VP1, type $O_1$ and
(f) anti-intact virus particle, type $C_1$.

The enzyme-linked immunosorbent assay was used to test each rod-coupled peptide (RCP) for reactivity with each of the defined antisera described above. RCPs were pre-coated with 10% horse serum, 10% ovalbumin and 1% Tween-80 in PBS, to block non-specific absorption of antibodies, for 1 hour at 37° C. Overnight incubation at 4° C. in antiserum diluted 1/40 in the preincubation mixture, was followed by 3 washes in 0.05% Tween-80/PBS. Reaction for 1 hour at 37° C. with the appropriate anti-rabbit IgG immunoglobulin coupled to horse radish peroxidase, diluted 1/50,000 in the preincubation mixture, was again followed by extensive washing in PBS/Tween to remove excess conjugate. The presence of antibody was detected by reaction for 45 min with a developing solution (40 mg orthophenylenediamine, 20 μl of hydrogen peroxide in 100 ml of phosphate buffer, pH 5.0), and the colour produced read in a Titertek Multiscan at 420 nm. After tests, peptides were washed three times at 37° C. in 8M urea containing 0.1% 2-mercaptoethanol and 0.1% sodium dodecyl sulphate, followed by several washes in PBS to remove all traces of bound antibody. The RCPs were then ready for further testing with different antisera.

Anti-intact virus particle sera were prepared by immunising rabbits with 50 μg of inactivated, purified virus in complete Freund's adjuvant. The animals were bled 3–4 weeks after the single vaccination. Anti-virus-subunit serum (rabbit) was prepared by immunizing 3 times, 3–4 weeks apart, with 10 μg of acid-disrupted purified virus, initially in complete Freund's and subsequently in incomplete Freund's adjuvant. The polypeptide VP1 was separated from the mixture of proteins obtained from urea disrupted, purified virus, by isoelectric focusing. (see Barteling, S. J., Wagenaar, F., Gielkens, A. L. J., J. Gen. Virol. 62, 357–361 (1982).) After elution from the gel with 8M urea and dialysis against PBS, antiserum was raised as described for 12S above. Antiserum for scan (c) was that used for scan (b), but after absorption with purified virus (1500 μg complete virus was incubated with 1 ml of serum for 72 hours at 4° C.), and all virus bound antibodies removed by centrifugation.

C. Identification of the virus particle-associated antigenic peptide

Of the four anti-intact virus particle sera tested, scans (a) and (b) show the extremes in the reactivity patterns found. Large quantitative differences in the response to an identical antigen preparation have been reported before, however, these scans highlight the variability possible in the antibody composition between sera. From an examination of scans (a), (b) and (c), antibody reactive with peptides numbers 146 and 147 are present in whole anti-intact virus sera, but absent after absorption with purified virus. These same antibodies are not observed in the anti-subunit sera, scan (d), and only weakly present in the anti-VP1 sera, scan (e). That some activity was found in the anti-VP1 sera, possibly accounts for the immunizing capacity, albeit weak, of the isolated protein. (see Kleid, D. G., et al., Science 214, 1125–1129 (1981).) It should be noted however that another anti-VP1 serum also tested, while retaining a strong activity in position number 148, showed nothing at positions numbers 146 and 147. The superimposition of scan (c) on scan (b) (absorbed compared to non-absorbed) shows that in addition to the loss of activity to peptides numbers 146 and 147, a reduction in activity to peptides numbers 5, 6 and 206 also occurred. Of these, activity to numbers 5 and 6 was not found in all the anti-intact virus sera tested, whilst number 206 activity was invariably present.

From these results, it is concluded that of the sequences found to be reactive, the pair at numbers 146 and 147, that is the hexapeptides Gly-Asp-Leu-Gln-Val-Leu (G - D - L - Q - V - L) and Asp-Leu-Gln-Val-Leu-Ala (D - L - Q - V - L - A), constitute the principal loci, with a lesser contribution from the locus at number 206, consistent with the observations of others. However, with respect to the loci at numbers 146-7, we do not distinguish between the two possibilities; one, that the active element is five amino acids long, i.e. the sequence common to both Asp-Leu-Gln-Val-Leu (D - L - Q - V - L); or two, that the active element is seven amino acids long, i.e. the combination of the two hexapeptides Gly-Asp-Leu-Gln-Val-Leu-Ala (G - D - L - Q - V - L - A).

EXAMPLE 2

A. Preparation of hexapeptides

The 212 amino acid sequence of VP1 (FMDV type $A_{10}$ or $A_{61}$ as given by Boothroyd, J. C. et al (1982) Gene, 17, 153–161 was subdivided into 207 hexapeptides. These hexapeptides were synthesised as described in Example 1 above with the exception that the side chain of arginine was protected by the p-methoxybenzene sulphonyl group.

B. Testing of hexapeptides

Antigenic profiles for the hexapeptides are shown in FIG. 3. The antisera used to produce the profiles were:
 (a) anti-intact virus particle type $A_{10}$
 (b) anti-intact virus particle as used in (a) after adsorption with purified complete FMDV type $A_{10}$.

The testing of the hexapeptide and preparation of the sera were essentially as described in Example 1.

C. Identification of virus-particle associated active element

By reasoning identical to that used in Example 1 it is concluded that the hexapeptides Gly-Asp-Leu-Gly-Ser-Ile (G - D - L - G - S - I) and Asp-Leu-Gly-Ser-Ile-Ala (D - L - G - S - I - A) are the principal loci for the antigenic determinant of the A-type of FMDV.

As in the case of FMD virus, type $O_1$, described in Example 1, we did not distinguish between these two sequences, and accordingly it is concluded that it is possible that the active sequence is five amino acids long, i.e. Asp-Leu-Gly-Ser-Ile (D - L - G - S - I), or that it is seven amino acids long, i.e. Gly-Asp-Leu-Gly-Ser-Ile-Ala (G - D - L - G - S - I - A).

EXAMPLE 3

A. Preparation of hexapeptides

The 210 amino acid sequence of VP1 (FMDV type $C_1$) as given by Cheung, A., et al (1983) J. Virol, 48, 4551–4559 Journal of Virology, 46, 311–316 (1983) was subdivided into 205 hexapeptides. These hexapeptides were synthesised as described in Example 2 above.

B. Testing of hexapeptides

Antigenic profiles for the hexapeptides are shown in FIG. 4. The antisera used to produce the profiles were:
 (a) anti-intact virus particle type $C_1$
 (b) anti-intact virus particle as used in (a) after absorption with purified complete FMDV type $C_1$.

The testing of the hexapeptide and preparation of the sera were essentially as described in Example 1.

C. Identification of virus-particle associated active element

By reasoning identical to that used in Example 1 it is concluded that the hexapeptide Asp-Leu-Ala-His-Leu-Thr (D - L - A - H - L - T) is the principal locus for the antigenic determinant of the C-type of FMDV.

These results clearly show the potential of a systematic scanning of a polypeptide sequence. They point out the likely location of the active determinant encompassed within the peptide with which Bittle, J. L. et al, Nature 298, 30–33 (1982), obtained the successful protection in guinea pigs to a subsequent challenge by FMDV.

EXAMPLE 4

A. Preparation of Peptides containing Replacement Amino Acids

The synthesis method of Example 1 was used to synthesize 120 hexapeptides, each consisting of five original amino acids of the antigenic hexapeptide G - D - L - Q - V - L (type $O_1$), the other amino acid being systematically replaced with each of the 20 possible naturally occurring genetically coded amino acids. This replacement was performed at each of the six positions in the peptide in turn. Thus, the 120 peptides comprised six copies of the original sequence and 114 variations of the original sequence, each of the 114 variations differing in only one amino acid from the original sequence. This strategy is illustrated diagrammatically in FIG. 5.

B. Testing of Peptides containing Replacement Amino Acids

The ELISA test of Example 1 was used to test the 120 peptides against an antiserum known to react with the original sequence. The results are shown in FIG. 6 and Table 1. In FIG. 6, the antibody-binding activity for each peptide is shown as a vertical line proportional to the ELISA extinction obtained. Within a group of 20 lines the left-hand line corresponds to the substitution of the original residue by alanine (A), and the right-hand line is for the substitution by tyrosine (Y). Lines in between are in alphabetic order according to the single letter code for each amino acid. Every group of twenty lines corresponds to the complete replacement set for one of the six N-terminal residue positions in the hexapeptide G - D - L - Q - V - L. It can be seen that the amino acids at certain positions in the sequence can be readily replaced without loss of antigenicity, whereas other positions cannot accept replacement without partial or complete loss of antigenicity. Those peptides containing replacements which result in retained antigenicity are candidates for use in vaccine manufacture.

C. The preparation and testing methods of A. and B. above were repeated with the antigenic hexapeptides G - D - L - G - S - I (type $A_{10}$) and D - L - A - H - L - T (type $C_1$) - see FIG. 5. The results are shown in Table 1.

EXAMPLE 5

The selected antigenic peptides of each of the three FMDV types were synthesized with a variety of linking amino acids at the N-terminal end and with the linking amino acid lysine at the C-terminal end. The amino acids in the links do not occur in those positions in the native sequences. The synthesized peptides were coupled to a protein carrier and combined with an adjuvant for the purpose of animal immunisation. The carrier was keyhole limpet hemocyanin (KLH) and the adjuvant was either an oil adjuvant or aluminium hydroxide gel.

Table 2 gives the results of serological tests on immunised rabbits. It shows that in each case the rabbit produced a significant amount of antibody able to react with FMDV and able to neutralise the infectivity of FMDV.

EXAMPLE 6

A protection test was carried out using guinea pigs as a model, since guinea pigs are susceptible to infection with FMDV. The peptide used for immunisation was C - G - D - L - Q - V - L - A - K, which is made up of the heptapeptide G - D - L - Q - V - L - A from FMDV type $O_1$ (residues 146–152), a cysteine linker at the N-terminal end and a lysine linker at the C-terminal end. To prepare the vaccine, the peptide was coupled to KLH using maleimidobenzoyl N-hydroxysuccinimide ester, which links the peptide to the KLH via the cysteine side chain.

The KLH-peptide conjugate was then absorbed to an aluminium hydroxide gel and used to vaccinate the guinea pigs at a dose of 100 µg peptide per animal. An unvaccinated group of guinea pigs served as controls.

The animals were challenged 21 days after the single vaccination.

The results of challenge were as follows:

|  | Vaccinated | Unvaccinated |
|---|---|---|
| Fully protected | 3 | 0 |
| Partially protected* | 2 | 0 |
| Unprotected** | 0 | 5 |
| TOTAL | 5 | 5 |

*1 to 6 lesion score points on a scale of 0 to 12.
**Greater than 6 lesion score points on a scale of 0 to 12.

These results show that the short peptide sequence used can stimulate the immune system of a model susceptible animal to give a protective response against challenge by virulent FMDV.

EXAMPLE 7

An example of the application of the present invention for diagnostic use is drawn from FIG. 2. This shows that ELISA testing using support-coupled peptides (SCPs) is an extremely strain-specific tool for detecting FMDV antibodies. Whole antisera to FMDV type $O_1$ reacted with hexapeptides 146, 147 and 206 derived from the FMDV type $O_1$ sequence, whereas antiserum to type $C_1$ did not react at all. Control testing on the antiserum to FMDV type $C_1$ showed that, likewise, specific reaction only occurred with peptides derived from the $C_1$ sequence. Testing of the SCPs with other non-FMDV-specific control sera, and hyperimmune sera to other FMDV types, has also shown that no reaction occurs.

Animal sera can therefore be tested on selected FMDV SCPs and a positive reaction is diagnostic of a previous exposure of the animal to FMDV antigen.

TABLE 1

Antibody-binding activities are shown for all peptides which gave an extinction significantly above the background. Values for each peptide are expressed as a percentage of the mean activity of the six parent sequences synthesised as a part of each replacement set. Underlined activities correspond to the values obtained for the parent sequence. No activity was detected when the antiserum used was prepared against the heterologous FMDV type.

| Parent sequence | Position in sequence | A | C | D | E | F | G | H | I | K | L |
|---|---|---|---|---|---|---|---|---|---|---|---|
| GDLGSI | 1 | 66 | 66 | 49 | 61 | 63 | <u>105</u> | 107 | 60 | 87 | 50 |
| Type $A_{10}$ | 2 |  |  | <u>118</u> |  |  |  |  |  |  | 28 |
|  | 3 |  |  |  |  |  |  |  |  |  | <u>88</u> |
|  | 4 | 29 |  |  |  |  | <u>98</u> |  |  |  |  |
|  | 5 | 12 |  |  |  |  | 27 |  |  |  |  |
|  | 6 | 47 | 96 | 28 | 81 | 87 |  |  | <u>85</u> | 108 | 108 |
| GDLQVL | 1 | 29 |  |  |  |  | <u>90</u> | 14 | 27 | 12 |  |
| Type $O_1$ | 2 | 22 | 21 | <u>143</u> | 95 | 110 | 28 | 65 |  | 12 | 65 |
| (48) | 3 |  |  |  |  |  |  |  |  |  | <u>79</u> |
|  | 4 |  |  | 64 | 14 |  |  |  |  |  |  |
|  | 5 | 62 |  | 33 | 52 |  |  |  | 26 |  | 29 |
|  | 6 |  |  |  |  |  |  |  |  |  | <u>119</u> |
| GDLQVL | 1 | 11 |  |  |  |  | <u>88</u> | 10 |  | 32 |  |
| Type $O_1$ | 2 | 37 | 12 | <u>136</u> | 92 | 137 | 52 | 62 | 21 | 87 | 81 |
| (31) | 3 |  |  |  |  |  |  |  |  |  | <u>88</u> |
|  | 4 | 60 |  | 117 | 52 |  |  |  |  | 68 |  |
|  | 5 | 52 |  | 40 | 63 | 42 |  |  | 56 | 82 | 68 |
|  | 6 |  |  |  |  |  |  |  |  |  | <u>105</u> |
| DLAHLT | 1 |  |  | <u>54</u> |  |  |  | 131 |  |  |  |
| Type $C_1$ | 2 |  |  |  |  |  |  |  |  |  | <u>133</u> |
|  | 3 | <u>108</u> |  |  |  |  |  |  |  |  |  |
|  | 4 | 272 | 68 | 367 | 307 | 159 |  | <u>95</u> |  | 253 | 50 |
|  | 5 |  |  |  |  |  |  |  |  |  | <u>93</u> |
|  | 6 |  |  |  |  |  |  |  |  |  |  |

TABLE 1-continued

Antibody-binding activities are shown for all peptides which gave an extinction significantly above the background. Values for each peptide are expressed as a percentage of the mean activity of the six parent sequences synthesised as a part of each replacement set. Underlined activities correspond to the values obtained for the parent sequence. No activity was detected when the antiserum used was prepared against the heterologous FMDV type.

| Parent sequence | Position in sequence | M | N | P | Q | R | S | T | V | W | Y |
|---|---|---|---|---|---|---|---|---|---|---|---|
| GDLGSI Type $A_{10}$ | 1 | 67 | 69 | 15 | 65 | 57 | 63 | 60 | 27 | 101 | 59 |
| | 2 | | | | | | | | | | |
| | 3 | | | | | | | | | | |
| | 4 | | | | | | | | | | |
| | 5 | | | | | | 106 | 97 | | | |
| | 6 | 97 | | | 108 | 162 | 97 | 72 | 55 | 23 | 19 |
| GDLQVL Type $O_1$ (48) | 1 | 32 | 34 | 41 | 29 | | 50 | | | | |
| | 2 | 15 | 58 | 10 | 69 | | 38 | 62 | | | |
| | 3 | | | | | | | | | | |
| | 4 | | 13 | | 80 | | | | | | |
| | 5 | 59 | | | 45 | | 49 | 43 | 89 | | |
| | 6 | | | | | | | | | | |
| GDLQVL Type $O_1$ (31) | 1 | 18 | 24 | 25 | 26 | | 77 | 14 | | | |
| | 2 | 37 | 89 | 49 | 80 | 29 | 63 | 104 | 60 | | 21 |
| | 3 | | | | | | | | | | |
| | 4 | 53 | 49 | | 102 | 10 | 45 | | | | |
| | 5 | 88 | 34 | | 106 | 33 | 91 | 98 | 81 | | 14 |
| | 6 | | | | | | | | | | |
| DLAHLT Type $C_1$ | 1 | | | | | | | | 135 | | |
| | 2 | | | | | | | | | | |
| | 3 | | | | | | | | | | |
| | 4 | 104 | 99 | | 224 | 101 | 238 | 262 | 94 | | 77 |
| | 5 | | | | | | | | | | |
| | 6 | | | | | | 30 | 117 | | | |

TABLE 2

Summary of immunogenicity data for a peptide from each of the 3 sero-types of FMDV. Results given for rabit sera after 2 vaccinations of peptide to carrier [100 μg dose]

| Virus of Origin | Active Peptide | N-Terminal link | C-Terminal link | Anti-whole virus ELISA titre ($\log_{10}$) | Micro-neutralization titre (MNT) ($\log_{10}$) |
|---|---|---|---|---|---|
| FMDV Type $O_1$ | GDLQVLA [146-152] | C— | —κ | 2.9 | 1.0 |
| | | CS— | —κ | 1.3 | 1.0 |
| | | CHS | —κ | 2.3 | 1.0 |
| FMDV Type $A_{10}$ | GDLGSIA [144-150] | C— | —κ | 1.4 | 1.0 |
| | | CS— | —κ | 2.3 | 1.7 |
| | | CHS— | —κ | 3.4 | 2.5 |
| FMDV Type $C_1$ | DLAHLTA [143-149] | C— | —κ | 3.1 | 1.8 |
| | | CS— | —κ | 2.0 | 1.3 |
| | | CHS | —κ | 2.8 | 1.9 |

1. N-Terminal and C-Terminal additions were used to facilitate the coupling of the active peptide to the carrier protein Keyhole Limpet Haemacyanin (KLH)
2. ELISA titres were obtained using purified homologous virus as the test antigen.
3. MNT tests were carried out as quantal assays using microtitre trays. Dilutions of serum were incubated with 100 median infectious doses of homologous infectious virus before inoculation onto BHK cell monolayers.

It will, of course, be recognised that many variations and modifications may be made to the detailed description of the method of the present invention given above without departing from the method of the invention as broadly described herein.

I claim:

1. A synthetic peptide which displays the antigenicity of the VP1 protein of foot-and-mouth disease virus, Type $O_1$, wherein said peptide is selected from amino acid sequences of the group consisting of:
   (i) G - D - L - Q - V - L - A;
   (ii) G - D - L - Q - V - L;
   (iii) D - L - Q - V - L - A;
   (iv) D - L - Q - V - L; and
   (v) antigenically acitve modified sequences based on any one of the sequences (i) to (iv) above in which one of the amino acids in said sequences (i) to (iv) above is replaced by another amino acid to provide said antigenically active modified sequences.

2. A synthetic peptide which displays the antigenicity of the VP1 protein of foot-and-mouth disease virus, Type $A_{10}$ ($A_{61}$), wherein said peptide is selected from amino acid sequences of the group consisting of:
   (i) G - D - L - G - S - I - A;
   (ii) G - D - L - G - S - I;
   (iii) D - L - G - S - I - A;
   (iv) D - L - G - S - I; and
   (v) antigenically active modified sequences based on any one of the sequences (i) to (iv) above in which one of the amino acids in said sequences (i) to (iv)

above is replaced by another amono acid to provide said antigenically active modified sequences.

3. A synthetic peptide which displays the antigenicity of the VP1 protein of foot-and-mouth disease virus, Type $C_1$, wherein said peptide is selected from amino acid sequence of the group consisting of:

(i) D - L - A - H - L - T - A;
(ii) D - L - A - H - L - T;
(iii) L - A - H - L - T - A;
(iv) L - A - H - L - T; and
(v) antigenically active modified sequences based on any one of the sequences (i) to (iv) above in which one of the amino acids in said sequences (i) to (iv) above is replaced by another amino acid to provide said antigenically active modified sequences.

4. A synthetic peptide according to claim 1, wherein said peptide is selected from hexapeptide sequences based on the formula:

$$G—D—L—Q—V—L$$
$$(1)\ (2)\ (3)\ (4)\ (5)\ (6)$$

in which:
G at position (1) is replaced by A, H, I, K, M, N, P, Q, S or T; or
D at position (2) is replaced by A, C, E, F, G, H, I, K, L, M, N, P, Q, R, S, T, V or Y; or
Q at position (4) is replaced by D, K, A, M, E, N, S or R; or
V at position (5) is replaced by A, D, E, F, I, K, L, M, N, Q, R, S, T or Y.

5. A synthetic peptide according to claim 2, wherein said peptide is selected from the group consisting of hexapeptide sequences baseed on the formula:

$$G—D—L—G—S—I$$
$$(1)\ (2)\ (3)\ (4)\ (5)\ (6)$$

in which:
G at position (1) is replaed by A, C, D, E, F, H, I, K, L, M, N, P, Q, R, S, T, V, W or Y; or
D at position (2) is replaced by L; or
G at position (4) is replaced by A; or
S at position (5) is replaced by T, G or A; or
I at position (6) is replaced by A, C, D, E, F, K, L, M, Q, R, S, T, V, W or Y.

6. A synthetic peptide according to claim 3, wherein said peptide is selected from the group consisting of hexapeptide sequences based on the formula:

$$D—L—A—H—L—T$$
$$(1)\ (2)\ (3)\ (4)\ (5)\ (6)$$

in which:
D at position (1) is replaced by H or V; or
H at position (4) is replaced by A, C, D, E, F, K, L, M, N, Q, R, S, T, V or Y; or
T at position (6) is replaced by S.

7. A vaccine for treating animals against infection by foot-and-mouth disease virus, comprising at least one synthetic peptide according to any one of claims 1 to 6.

8. A vaccine according to claim 7, further comprising a physiologically acceptable carrier and/or adjuvant.

9. A vaccine according to claim 8, wherein said at least one synthetic peptide is linked to said physiologically acceptable carrier.

10. A method of treating animals against infection by foot-and-mouth disease virus, which comprises administering to said animals a vaccine according to claim 7.

11. A diagnostic or other immunological testing composition for detecting the presence of foot-and-mouth disease virus or of antibodies against foot-and-mouth disease virus in an animal, comprising at least one synthetic peptide according to any one of claims 1 to 6 as an antigenically active component of said composition.

12. A vaccine according to claim 7, wherein said at least one synthetic peptide is linked to a physiologically acceptable carrier.

13. A method of treating animals against infection by foot-and-mouth disease virus, which comprises administering to said animals a vaccine according to claim 8.

14. A method of treating animals against infection by foot-and-mouth disease virus, which comprises administering to said animals a vaccine according to claim 9.

15. The synthetic peptide according to claim 1, 2, 3, 4, 5, or 6, additionally including one or more additional amino acids either at the carboxyl end, at the amino end or at both the carboxyl and the amino ends of said sequence, wherein said one or more additional amino acids do not substantially alter the antigenicity of said synthetic peptide.

16. A vaccine for treating animals against infection by foot-and-mouth disease virus, comprising at least one synthetic peptide according to claim 15.

17. A method of treating animals against infection by foot-and-mouth disease virus, which comprises administering to said animals a vaccine according to claim 16.

18. A diagnostic or other immunological testing composition for detecting the presence of foot-and-mouth disease virus or of antibodies against foot-and-mouth disease virus in an animal, comprising at least one synthetic peptide according to claim 15, as an antigenically active component of said composition.

* * * * *